United States Patent [19]

Erhardt et al.

[11] Patent Number: 4,556,668

[45] Date of Patent: Dec. 3, 1985

[54] ETHYLENEDIAMINE DERIVATIVES OF ARYLOXYPROPANOLAMINE ARYL ESTERS HAVING VARIOUS MEDICINAL PROPERTIES

[75] Inventors: Paul W. Erhardt, Long Valley, N.J.; Chi Woo, Vernon Hills, Ill.

[73] Assignee: American Hospital Supply Corporation, Evanston, Ill.

[21] Appl. No.: 514,120

[22] Filed: Jul. 15, 1983

[51] Int. Cl.$^4$ .................. C07D 213/74; A61K 31/44
[52] U.S. Cl. ................................ 514/353; 514/352; 546/297; 546/300; 546/304; 546/306
[58] Field of Search ............. 546/304, 306, 297, 300; 424/263; 514/352, 353

[56] References Cited

U.S. PATENT DOCUMENTS 4,356,322 10/1982 Lehmann et al. ............... 564/348
4,387,103 6/1983 Erhardt et al. .................. 514/538

FOREIGN PATENT DOCUMENTS 0042593 12/1981 European Pat. Off. ........... 548/371
1957706 5/1970 Fed. Rep. of Germany ...... 560/48
2844497 6/1979 Fed. Rep. of Germany ...... 564/348

OTHER PUBLICATIONS

March, Advanced Organic Chemistry, Reactions, Mechanisms and Structure, Second Edition, pp. 459–463, McGraw Hill Pub.

Primary Examiner—Alan L. Rotman
Attorney, Agent, or Firm—Donald L. Barbeau; Gildo E. Fato

[57] ABSTRACT

Described herein are compounds of the formula

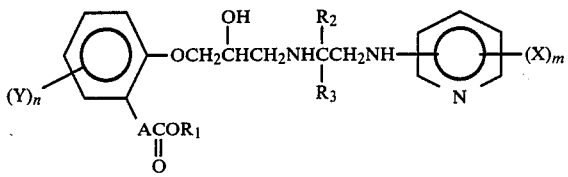

wherein $R_1$ is alkyl of from 1 to about 5 carbon atoms, alkenyl of from 2 to about 5 carbon atoms, alkynyl of from 3 to about 5 carbon atoms, cycloalkyl of from 3 to about 7 carbon atoms, alkylcarboxymethyl wherein the alkyl portion is from 1 to about 5 carbon atoms, arylcarboxymethyl wherein the aryl portion is from 6 to about 10 carbon atoms, aryl of from 6 to about 10 carbon atoms, or aralkyl wherein the alkyl portion is from 1 to about 5 carbon atoms and the aryl portion is from about 6 to about 10 carbon atoms; $R_2$ and $R_3$ are independently hydrogen or alkyl of from 1 to about 3 carbon atoms; X is alkyl of from 1 to about 4 carbon atoms, alkenyl of from 2 to about 4 carbon atoms, alkynyl of 3 or 4 carbon atoms, alkoxy of from 1 to about 4 carbon atoms, hydroxyalkyl of from 1 to about 4 carbon atoms, alkylamino of from 1 to about 4 carbon atoms, halogen, amino, nitro, hydroxy, acetamido, or cyano; m is an integer from 0 to about 3, A is a direct bond, alkylene of from 1 to about 5 carbon atoms, or alkenylene of from 2 to about 5 carbon atoms, Y is alkyl of from 1 to about 4 carbon atoms, alkenyl of from 2 to about 4 carbon atoms, alkynyl of 3 or 4 carbon atoms, alkoxy of from 1 to about 4 carbon atoms, hydroxyalkyl of from 1 to about 4 carbon atoms, alkylamino of from 1 to about 4 carbon atoms, halogen, amino, nitro, hydroxy, acetamido, or cyano; n is an integer from 0 to about 3; and the pharmaceutically acceptable salts thereof.

10 Claims, No Drawings

ETHYLENEDIAMINE DERIVATIVES OF ARYLOXYPROPANOLAMINE ARYL ESTERS HAVING VARIOUS MEDICINAL PROPERTIES

BACKGROUND OF THE INVENTION

The therapeutic and prophylactic uses of compounds which block sympathetic nervous stimulation of $\beta$-adrenergic receptors in the heart, lungs, vascular system and other organs are well documented. Typically, such compounds are administered therapeutically to patients suffering from ischemic heart disease or myocardial infarction for the purpose of reducing heart work, i.e., heart rate and contractile force. Reducing heart work reduces oxygen demand, and may also actually increase oxygen supply. Thus reducing heart work can aid in the prevention of further tissue damage and can relieve angina pectoris.

$\beta$-Adrenergic stimulation may also aggravate or cause arrhythmias because of increased levels of catecholamines. Thus $\beta$-blocking agents may be employed to reduce the risks of arrhythmias.

Compounds in accordance with the present invention selectively block $\beta$-adrenergic receptors in various organs. Beta receptors in the heart are generally referred to as $\beta_1$ receptors, and those associated with vasodilation and bronchodilation are $\beta_2$ receptors. Selective $\beta$-blockers are preferred for the treatment of cardiac disorders, because they may have less potential to cause hypertension or bronchoconstriction. A number of $\beta_1$ selective adrenergic blocking agents have been discovered [Smith, L. H., *J. Appl. Chem.* Biotechnol., 28, 201–202 (1978)]. Most such compounds are structural variations of 1-amino-3-aryloxy-2-propanol.

Heretofore, the emphasis in $\beta$-blocker research has been to develop compounds which can be administered to cardiac patients over long periods of time. However, often it is desirable in the critical care setting to quickly reduce heart work or improve rhythmicity during a cardiac crisis, e.g., during or shortly after a myocardial infarction. Conventional $\beta$-blocking agents can be employed for such treatment, but their duration of action may be much longer than desired by the physician. A $\beta$-blocking agent possessing a long duration of action does not allow precise control of heart work or prompt reversal of the $\beta$-blocking effect, which may be required in a critical care setting. For instance, if heart output becomes dangerously low, it is desirable to quickly reduce or eliminate $\beta$-blocking activity. The lingering activity of available $\beta$-blocking agents can be counterproductive and can greatly complicate the therapeutic decisions required of the physician during such critical care of cardiac patients.

Accordingly, there is a need for a pharmaceutical preparation and method of treatment, employing a cardioselective $\beta$-adrenergic blocking agent having a short duration of action.

Compounds of the present invention are also useful for the treatment of glaucoma or lowering of intraocular pressure by topical administration of the compounds to the eye. Compounds with short duration in the systemic circulation, but with good stability in ocular fluid, are particularly useful since they have a low potential for producing systemic side effects.

Glaucoma is a condition of the eye characterized by increased intraocular pressure. Untreated, the condition can eventually lead to irreversible retinal damage and blindness. Conventional therapy for glaucoma has involved topical administration of pilocarpine and/or epinephrine, administered to the eye several times daily.

The use of various $\beta$-blocking agents to lower intraocular pressure is well documented. For example, U.S. Pat. No. 4,195,085 to Stone discloses a method for treatment of glaucoma by the optical administration of a $\beta$-blocking compound, timolol maleate. U.S. Pat. No. 4,127,674 discloses a method of treating glaucoma with labetalol, a known antagonist of both alpha and beta adrenergic receptors. However, these methods also possess significant drawbacks, in that the absorption of the $\beta$-blocking compound into the systemic circulation can cause undesirable side effects. Such side effects result from prolonged $\beta$-blocking action on the heart, bronchioles and blood vessels. For example, according to *Physicians' Desk Reference*, Charles E. Baker, Jr., 35th Edition, 1981, p. 1233, adverse reactions to the topical use of timolol maleate can include bronchospasm and heart failure, as well as cardiac conduction defects. Accordingly, there is a need for a method of treatment for glaucoma or for lowering intraocular pressure which is relatively free of unwanted systemic side-effects.

In several copending U.S. patent applications, Ser. No. 211,340 filed Nov. 28, 1980 now abandoned, refiled June 21, 1982 as Ser. No. 390,629, now U.S. Pat. No. 4,450,173; issued May 22, 1984; Ser. No. 276,658 filed June 23, 1981 now U.S. Pat. No. 4,402,974; issued Sept. 6, 1983; and Ser. No. 320,772 filed Nov. 12, 1981 by the owner of the present application, the synthesis and pharmacology of a number of aryloxypropanol amines are described. This work demonstrated that if certain ester and alkyl ester groups are placed on the aryl group that short-acting $\beta$-blocking compounds can be obtained; compounds varying in $\beta$-blocking potency and cardioselectivity depending upon the position of the ester on the aryl group.

SUMMARY OF THE INVENTION

The present invention relates to compounds of the formula

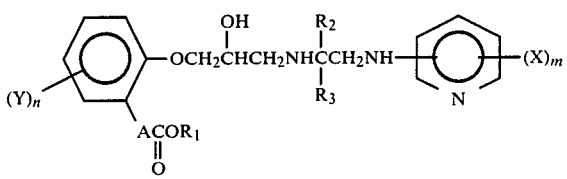

wherein $R_1$ is alkyl of from 1 to about 5 carbon atoms, alkenyl of from 2 to about 5 carbon atoms, alkynyl of from 3 to about 5 carbon atoms, cycloalkyl of from 3 to about 7 carbon atoms, alkylcarboxymethyl wherein the alkyl portion is from 1 to about 5 carbon atoms, arylcarboxymethyl wherein the aryl portion is from 6 to about 10 carbon atoms, aryl of from 6 to about 10 carbon atoms, or aralkyl wherein the alkyl portion is from 1 to about 5 carbon atoms and the aryl portion is from 6 to about 10 carbon atoms; $R_2$ and $R_3$ are independently hydrogen or alkyl of from 1 to about 3 carbon atoms; X is alkyl of from 1 to about 4 carbon atoms, alkenyl of from 2 to about 4 carbon atoms, alkynyl of 3 or 4 carbon atoms, alkoxy of from 1 to about 4 carbon atoms, hydroxyalkyl of from 1 to about 4 carbon atoms, alkylamino of from 1 to about 4 carbon atoms, halogen, amino, nitro, hydroxy, acetamido, or cyano; m is an integer from 0 to about 3, A is a direct bond, alkylene of from 1 to about 5 carbon atoms, or alkenylene of from 2 to about 5 carbon atoms, Y is alkyl of from 1 to about 4 carbon atoms, alkenyl of from 2 to about 4 carbon atoms, alkynyl of 3 or 4 carbon atoms, alkoxy of from 1 to about 4 carbon atoms, hydroxyalkyl of from 1 to about 4 carbon atoms, alkylamino of from 1 to about 4 carbon atoms, halogen, amino, nitro, hydroxy, acetamido, or cyano; n is an integer from 0 to about 3; and the pharmaceutically acceptable salts thereof.

DETAILED DESCRIPTION OF THE INVENTION

The present invention relates to compounds of the formula

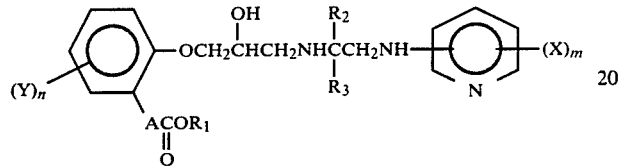

wherein $R_1$ represents lower alkyl of straight or branched carbon chains from 1 to about 5 carbon atoms, lower cycloalkyl of from 3 to about 7 carbon atoms, lower alkenyl of from 2 to about 5 carbon atoms, lower alkynyl of from 3 to about 5 carbon atoms, lower alkyl carboxymethyl in which the alkyl portion contains from 1 to about 5 carbon atoms, aryl carboxymethyl in which the aryl portion contains from 6 to about 10 carbon atoms, aryl of from 6 to about 10 carbon atoms or aralkyl wherein the alkyl portion contains from 1 to about 6 carbon atoms and the aryl portion represents substituted or unsubstituted monocyclic or polycyclic aromatic or heterocyclic ring systems of from 6 to about 10 carbon atoms; A represents a direct bond between the ester group and the phenyl group, lower alkylene of from 1 to about 5 carbon atoms, or alkenylene of from 2 to about 5 carbon atoms; Y and X are independent lower alkyl of from 1 to about 5 carbon atoms, lower alkenyl of from 2 to about 5 carbon atoms, lower alkynyl of from 2 to about 5 carbon atoms, lower alkoxy of from 1 to about 5 carbon atoms, halogen, acetamido, amino, nitro, lower alkylamino of from 1 to about 5 carbon atoms, hydroxy, lower hydroxyalkyl of from 1 to about 5 carbon atoms, and cyano. Such compounds may be administered as their pharmaceutically acceptable acid addition salts, e.g., as the hydrochloride, sulfate, phosphate, gluconate, tartrate, etc.

The ester substituent, $R_1$, in preferred compounds, is lower alkyl such as methyl, ethyl, n-butyl, n-pentyl, and the like; lower alkenyl such as ethenyl, 2-propenyl, 2-methyl-3-butenyl and the like, lower alkynyl such as propargyl, methylpropargyl and the like, or lower cycloalkyl of from 3 to about 5 carbon atoms such as cyclopropyl, cyclopentyl, 2-methylcyclopropyl, and the like.

In particularly preferred compounds, the ester substituent $R_1$ is methyl or ethyl; A is a direct bond, lower alkylene of from 1 to about 5 carbon atoms, such as methylene, ethylene, butylene and the like, or lower alkenylene of from 2 to about 5 carbon atoms, such as ethenylene, 2-propenylene, 2-butenylene, and the like.

Compounds of the present invention exist as two stereoisomers due to the presence of an asymmetric carbon atom. This invention includes either stereoisomeric form, as well as racemic mixtures. For compounds in which A represents alkenyl or alkenylene, both cis and trans isomers are within the scope of the invention.

The compounds described herein may be prepared by any suitable procedure. Compounds prepared as the acid addition salts may be converted to the free base by reaction with an appropriate base such as sodium carbonate or sodium bicarbonate. The compounds are advantageously prepared by reacting an appropriate ortho derivative of phenol or substituted phenol with epichlorohydrin in the presence of a base to form a 1,2-epoxy-3-aryloxypropane derivative according to the following reaction:

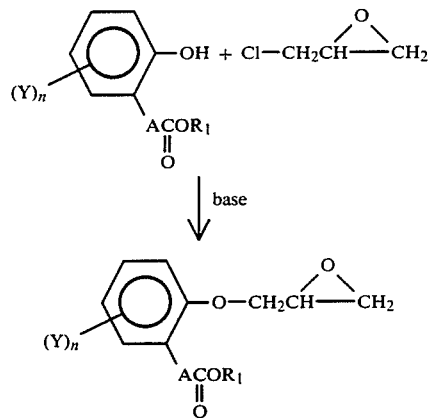

wherein $R_1$, A, Y, and n are defined as hereinbefore. The 1,2-epoxy-3-aryloxy-propane so prepared may then be reacted with an ethylediamine to form the desired product:

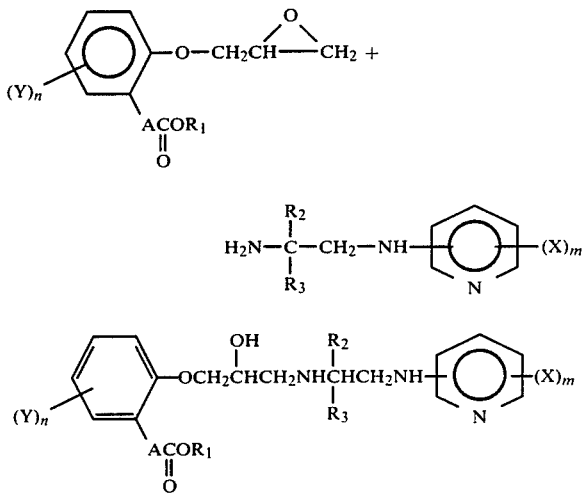

wherein $R_1$, $R_2$, $R_3$, A, Y, X, m, and n are defined as hereinbefore. This reaction is preferably conducted in an alcoholic solvent identical to the ester adduct to prevent alcoholysis side reactions, e.g., when $R_1$ is methyl, the reaction solvent is preferably methanol.

The phenol derivatives used as starting materials in the reaction scheme described above are generally commercially available compounds or may be prepared by methods known in the art.

The syntheses of some of the starting materials for compounds of the present invention are described in copending U.S. patent application Ser. No. 211,345 now U.S. Pat. No. 4,387,103 which is hereby incorporated by reference.

The pyridine-containing diamines and derivatives are generally commercially available, or may be prepared by conventional methods such as those shown below:

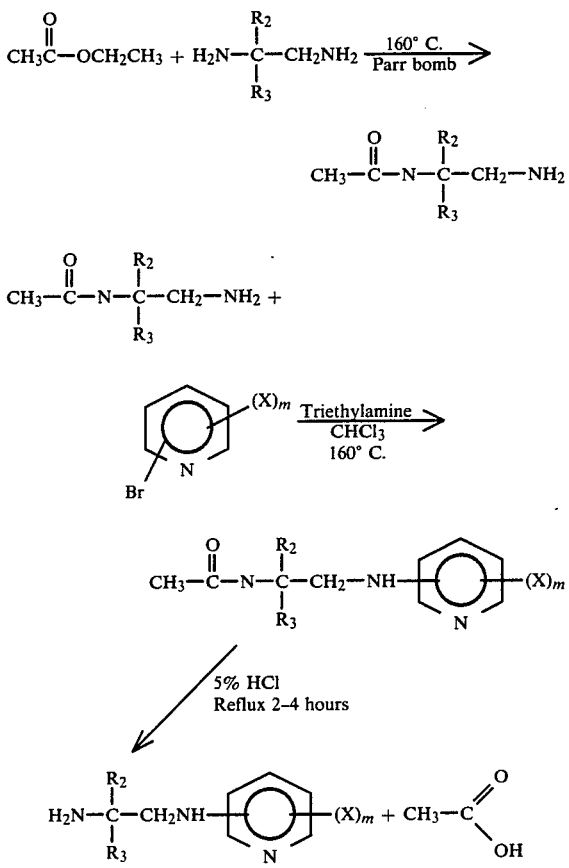

The positioning of the bromine on the pyridine, i.e., ortho, meta, para, will direct the nucleophilic substitution of the amine to ortho, meta, or para positions in the nucleus, respectively. Moreover, the HCl-adduct so obtained can be used directly in the reaction with the 1,2-epoxy-3-aryloxy-propane, or can first be freed of HCl by extraction in aqueous base.

When used for the treatment of cardiac disorders, the compounds of this invention are advantageously administered parenterally, e.g., by intravenous injection or intravenous infusion. Formulations for intravenous injection preferably include the active compound as a soluble acid addition salt in a properly buffered isotonic solution.

The dosage administered to a patient and the duration of infusion will depend upon the patient's needs and the particular compounds employed. For short periods of infusion, e.g., less than about three hours, the duration of effect is thought to be determined by both metabolic effects and distribution phenomena. For relatively long periods of infusion, e.g., greater than about three hours, the duration of effect is thought to depend largely on metabolic effects. Dosages of about 0.001 to about 100 mg. per kg. of body weight per hour are generally employed with preferred dosages ranging from about 0.01 to about 10 mg. per kg. of body weight per hour.

When used for the treatment of glaucoma, the compounds of this invention are advantageously administered topically to the eye in the form of a solution, ointment, or solid insert such as is described in U.S. Pat. No. 4,195,085. Formulations may contain the active compound, preferably in the form of a soluble acid addition salt, in amounts ranging from about 0.01 to about 10% by wt., preferably from about 0.5% to about 5% by wt. Unit dosages of the active compound can range from about 0.001 to about 5.0 mg., preferably from about 0.05 to about 2.0 mg. The dosage administered to a patient will depend upon the patient's needs and the particular compounds employed.

Carriers used in the preparations of the present invention are preferably non-toxic pharmaceutical organic or inorganic compositions such as water; mixtures of water and water-miscible solvents, such as lower alcohols; mineral oils; petroleum jellies; ethyl cellulose; polyvinylpyrrolidone and other conventional carriers. In addition, the pharmaceutical preparations may also contain additional components such as emulsifying, preserving, wetting and sterilizing agents. These include polyethylene glycols 200, 300, 400 and 600, carbowaxes 1,000; 1,500; 4,000; 6,000 and 10,000, bacteriocidal components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The method of treatment of this invention advantageously involves the topical administration of eye drops containing the active compound. Formulations for eye drops preferably include the active compound as a soluble acid addition salt in a properly buffered, sterile, aqueous isotonic solution.

The compounds of the present invention are ester group-containing β-blockers that have a selective, localized, β-blocking effect in the eye after topical administration. Such compounds are thought to be rapidly metabolized by plasma and/or liver esterases into inactive byproducts, upon entering the systemic circulation. It has been discovered that compounds such as these are relatively stable in ocular fluids, i.e., lacrimal fluids and aqueous humor. Consequently, such compounds are useful for the treatment of glaucoma or for lowering intraocular pressure since they remain stable when topically applied to the eye but rapidly metabolize when subsequently absorbed into the systemic circulation.

Some of the compounds break down in the aqueous humor more rapidly than others. Such compounds may advantageously be employed when only a temporary reduction in intraocular pressure is desired, say for diagnostic procedures. Longer-acting compounds are generally used for effecting longer-term reductions in intraocular pressure, such as is desired when treating chronic glaucoma. Thus, the compounds of the present invention provides a very useful therapeutic alternative for the treatment of glaucoma or for lowering intraocular pressure.

Beta Blocking Activity In Vitro

Compounds of the present invention are tested for β-blocking activity in vitro using guinea pig right atria and guinea pig tracheal strips mounted in a tissue bath containing oxygenated (95% $O_2$-5% $CO_2$) Krebs physiological salt solution at 37° C. Each tissue is suspended between a fixed glass rod and a Statham Universal Transducer connected to a Beckman recorder. Atria were allowed to beat spontaneously under a loading tension of approximately 0.5 gm. Intrinsic depressant or stimulant activity is determined for each compound by progressively increasing concentrations in the tissue baths at 60-minute intervals. Tissues are not washed between increments. The maximum concentration showing little or no cardiodepressant activity is chosen for blockade experiments. Changes in rate in response to isoproterenol, a standard β-receptor agonist, is measured in the absence and presence of test compounds. Spiral strips of guinea pig trachea are suspended under 5 gm resting tension and incubated with phentolamine, tropolone and cocaine. Active tension is generated by addition of carbachol ($3.0 \times 10^{-7}$M) and decreases in tension in response to isoproterenol are quantitated. Cumulative concentration-response curves are produced with isoproterenol both before and after 60-minute incubation of test compounds with atria and trachea. Compounds with β-blocking activity shift concentration-response curves to the right. The blocking potency is estimated by computing $pA_2$ values ($-\log K_B$) by the method of Furchgott, the Pharmacological Differentiation of Adrenergic Receptors, *Ann. N.Y. Acad. Sci.*, 139: 553–570 (1967). Comparison of blockade of right atrial and tracheal responses to isoproterenol permits assessment of cardioselectivity of test compounds; i.e., cardioselective compounds are relatively more effective in blocking atrial rate than tracheal force response to isoproterenol. The degree of cardioselectivity was estimated from the ratio, $K_B$ trachea/$K_B$ atria ($10^{(pA2atria-pA2trachea)}$). A ratio greater than one indicates cardioselectivity. Test drugs are dissolved in distilled water and added to the bath (30 ml) in a volume of 10 or 100 μl.

Duration and Potency of Beta-Blocking Action in Vivo

The duration of β-blockade is determined In vivo using pentobarbital-anesthetized dogs instrumented for measurement of heart rate using a Beckman cardiotachometer triggered electronically by a phasic aortic blood pressure signal. Both vagus nerves are severed in the cervical region and the animals are mechanically ventilated. The experimental design used employs a 3-hour infusion of test compound. Bolus doses of isoproterenol (0.5 μg/kg) are used to assess the degree of β-blockade and recovery from β-blockade after determination of the infusion. The doses are spaced at 10-minute intervals and are given before, during and following the infusion of test compounds. The infusion rate is adjusted so that at the end of the 3-hour infusion period the degree of isoproterenol inhibition averaged about 50% of control. Following termination of blocker infusion, percent recovery from β-blockade is computed and the time associated with 80% recovery estimated.

The present invention is further illustrated by the following examples which are not intended to be limiting.

EXAMPLE I

Methyl 2[2-Hydroxy-3-[2-[2-(5-nitropyridinyl)amino]ethyl-]aminopropoxy benzoate

This example describes the synthesis of a compound having the formula

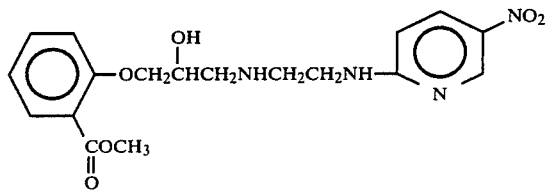

A quantity of 3.64 of 2(2-aminoethylamino)-5-pyridine (0.02 mole) and 4.16 g of methyl 2-(2,3-epoxypropoxy)-benzoate (0.024 mole) were reacted in methanol for 16 hours at 25° C. The methanol was then removed under reduced pressure, leaving an oil which was dissolved in 100 ml methylene chloride, washed twice with 100 ml of water, and dried over anhydrous magnesium sulfate. Evaporation of the methylene chloride left 8.3 g of an oil, which was combined with 2.68 g of oxalic acid in 100 ml methanol, and diluted with 100 ml of ether. The product crystallized slowly at 3° C. to provide 2.8 g (32%) of product which had a melting point of 212.8° C. The IR and NMR spectra were consistent with the assigned structure, and the elemental analysis was consistent with the empirical formula (C, H, N, 52.61, 5.53, 12.91).

EXAMPLE II

The compound of Example I was tested for in vitro β-blocking potency and duration of action as described hereinabove. The compound had a $pA_2$ value of 7.5 in the atria, a $pA_2$ value of 7.1 in the trachea, and a cardioselectivity of 2.5. The in vivo duration of action was 15±6 minutes.

The present invention has been described in specific detail and with reference to its preferred embodiments; however, it will be understood by those skilled in the art that modifications can be made thereto without departing from the spirit and scope thereof.

We claim:

1. A compound having the formula

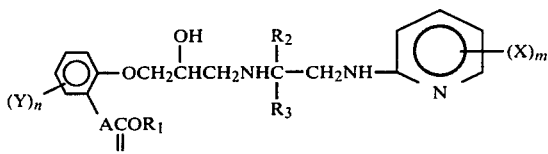

wherein $R_1$ is alkyl of from 1 to 5 carbon atoms, alkenyl of from 2 to 5 carbon atoms, cycloalkyl of from 3 to 7 carbon atoms; $R_2$ and $R_3$ are independently hydrogen or an alkyl of from 1 to 3 carbon atoms; X is alkyl of from 1 to 4 carbon atoms, alkenyl of from 2 to 4 carbon atoms, halogen, amino, nitro, hydroxy; m is an integer from 0 to 1, A is a direct bond, Y is alkyl of from 1 to 4 carbon atoms, alkenyl of from 2 to 4 carbon atoms, halogen, amino, nitro, hydroxy; n is an integer from 0 to 1; and the pharmaceutically acceptable salts thereof.

2. A compound in accordance with claim 1 wherein n is 0; $R_1$ is alkyl of from 1 to 5 carbon atoms, alkenyl of from 2 to 5 carbon atoms; and $R_2$ and $R_3$ are independently hydrogen or methyl.

3. A compound having the formula

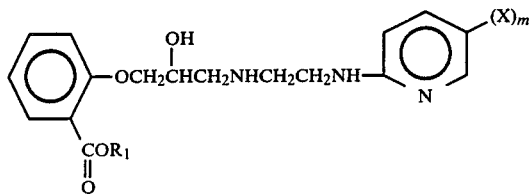

wherein X is alkyl of from 1 to 4 carbon atoms or nitro, $R_1$ is alkyl of from 1 to 5 carbon atoms, and m is 0 or 1.

4. A compound in accordance with claim 3 wherein n is 0; $R_1$ is methyl, ethyl, or propyl, and m is 1.

5. A compound in accordance with claim 3 wherein n is 0; $R_1$ is methyl or ethyl; and m is 0.

6. A compound in accordance with claim 4 wherein X is nitro; and $R_2$ and $R_3$ are independently hydrogen or methyl.

7. A compound in accordance with claim 1 wherein n is 0; $R_1$ is methyl or ethyl; $R_2$ and $R_3$ are independently hydrogen or methyl; and m is 1.

8. A compound in accordance with claim 3 which is Methyl 2[2-Hydroxy-3-[2-[2-(5-nitropyridinyl)amino]ethyl]aminopropoxy benzoate.

9. A pharmaceutical composition useful in the treatment of ischemic heart disease, myocardial infarction, arrhythmias or angina pectoris comprising an effective amount of a compound in accordance with claim 1 in admixture with a pharmaceutical carrier or diluent.

10. A pharmaceutical composition useful in the lowering of intraocular pressure comprising an effective amount of a compound in accordance with claim 1 in admixture with a pharmaceutical carrier or diluent.

* * * * *